United States Patent

Breitscheidel et al.

[11] Patent Number: 5,696,048
[45] Date of Patent: Dec. 9, 1997

[54] COBALT CATALYSTS

[75] Inventors: Boris Breitscheidel, Fulda; Peter Polanek, Weinheim; Guido Voit, Schriesheim; Tom Witzel, Ludwigshafen; Gerd Linden, Heidelberg; Michael Hesse, Schifferstadt, all of Germany

[73] Assignee: BASF Aktiengesellschaft, Ludwigshafen, Germany

[21] Appl. No.: 641,278

[22] Filed: Apr. 30, 1996

[30] Foreign Application Priority Data

May 9, 1995 [DE] Germany .......................... 195 16 845.3
Jul. 11, 1995 [DE] Germany .......................... 195 25 187.3

[51] Int. Cl.[6] .................................................. B01J 27/185
[52] U.S. Cl. .................................................. 802/213
[58] Field of Search .................................................. 802/213

[56] References Cited

U.S. PATENT DOCUMENTS

| | | |
|---|---|---|
| 4,598,058 | 7/1986 | Frank et al. .............................. 502/183 |
| 5,039,648 | 8/1991 | Horn . |
| 5,254,738 | 10/1993 | Koehler et al. .......................... 564/491 |
| 5,536,591 | 7/1996 | Breitscheidel et al. . |
| 5,536,691 | 7/1996 | Breitscheidel et al. ............... 502/213 |

FOREIGN PATENT DOCUMENTS

| | | |
|---|---|---|
| 332760 | 7/1989 | European Pat. Off. . |
| 0 445 589 | 9/1991 | European Pat. Off. . |
| 3403377 | 1/1985 | Germany . |
| 43 25 847 | 2/1995 | Germany . |

*Primary Examiner*—Glenn A. Caldarola
*Assistant Examiner*—Tanaga Anne Boozer
*Attorney, Agent, or Firm*—John H. Shurtleff

[57] ABSTRACT

Cobalt catalysts whose catalytically active composition comprises from 55 to 98% by weight of cobalt, from 0.2 to 15% by weight of phosphorus, from 0.2 to 15% by weight of manganese and from 0.05 to 5% by weight of alkali metal, calculated as oxide, are prepared by calcining the catalyst composition, reducing it at final temperatures of from 200° to 400° C. in a stream of hydrogen and subsequently surface-oxidizing it by treatment in a stream of air at final temperatures of from 20° to 60° C. and can be used in a process for hydrogenating organic nitriles and/or imines.

9 Claims, No Drawings

COBALT CATALYSTS

The present invention relates to novel cobalt catalysts whose catalytically active composition comprises cobalt, phosphorus, manganese and alkali metal and which are, after calcination, reduced in a stream of hydrogen at final temperatures of from 200° to 400° C. and are subsequently surface-oxidized by treatment in a stream of air at final temperatures of from 20° to 60° C.

EP-A-445 589 discloses hydrogenation catalysts whose catalytically active composition comprises from 20 to 95% by weight of cobalt oxide, from 0.5 to 60% by weight of oxides of the metals manganese, nickel, iron, chromium, molybdenum, tungsten or phosphorus and from 0.5 to 20% by weight of oxides of the alkali metal or alkaline earth metal group, the rare earth group scandium or yttrium.

DE-A-34 03 377 discloses shaped catalyst compositions comprising metallic cobalt and/or nickel and containing less than 0.1% by weight of alkali metal and/or alkaline earth metal oxides, and which have been prepared by reduction at less than or equal to 500° C. The shaped catalyst compositions have a compressive hardness of more than 300 kp/cm$^2$.

However, the above catalysts have the disadvantage that they are not sufficiently base-stable to ensure a long life in a basic medium.

DE-A 43 25 847 describes cobalt-containing, base-stable catalysts whose catalytically active composition comprises from 55 to 98% by weight of cobalt, from 0.2 to 15% by weight of phosphorus, from 0.2 to 15% by weight of manganese and from 0.2 to 15% by weight of alkali metal and which are prepared by two calcination steps at final temperatures of from 550° to 750° C. and from 800° to 1000° C. These cobalt catalysts have a cutting hardness of greater than or equal to 10N after carrying out an autoclave test for determining the base stability and, on the basis of experience, have a life of >3000 hours, but at most 5000 hours, for reactions in basic media.

However, catalyst lives of >5000 hours are necessary for economically carrying out reactions in basic media, eg. the hydrogenation of organic nitriles and/or imines.

It is an object of the present invention to find a solution to the abovementioned disadvantages, in particular to develop cobalt-containing catalysts which have a base stability sufficiently high for lives of >5000 hours to be achieved for reactions in basic media.

We have found that this object is achieved by cobalt catalysts whose catalytically active composition comprises from 55 to 98% by weight of cobalt, from 0.2 to 15% by weight of phosphorus, from 0.2 to 15% by weight of manganese and from 0.05 to 5% by weight of alkali metal, calculated as oxide, wherein the calcined catalysts are reduced in a stream of hydrogen at a final temperature of from 200° to 400° C. and are subsequently surface-oxidized by treatment in a stream of air at final temperatures of from 20° to 60° C., and a process for hydrogenating nitriles and/or imines using these cobalt catalysts.

The catalytically active composition of the cobalt catalysts of the invention comprises from 55 to 98% by weight of cobalt, preferably from 75 to 95% by weight of cobalt, particularly preferably from 85 to 95% by weight of cobalt, from 0.2 to 15% by weight of phosphorus, preferably from 0.5 to 10% by weight of phosphorus, particularly preferably from 1 to 6% by weight of phosphorus, from 0.2 to 15% by weight of manganese, preferably from 2 to 10% by weight of manganese, particularly preferably from 3 to 8% by weight of manganese, and from 0.05 to 5% by weight of alkali metal, preferably from 0.1 to 3% by weight of alkali metal, particularly preferably from 0.13 to 1% by weight of alkali metal, calculated as oxide.

Suitable alkali metals are preferably, lithium, sodium, potassium and/or cesium, particularly preferably sodium and/or potassium.

The cobalt catalysts of the invention can be prepared as follows:

From a solution of a cobalt salt, preferably an inorganic cobalt salt, and, if desired, the desired promoters manganese, phosphorus and/or alkali metals in the form of their water-soluble salts (normally pH<7), a mixture of the main constituents of the catalyst can be precipitated in the form of the carbonates, hydroxides or oxides by addition of an alkaline solution. The alkaline solution can be prepared by dissolving, for example, alkali metal carbonate or hydroxides, ammonia, ammonium carbonate or ammonium hydrogen carbonate or similar basic salts in water. The concentrations of both the metal salt and the precipitant solution should be set so that the resulting precipitation slurry can still be stirred. If the promoters are not coprecipitated in this step, they can be introduced in one of the process stages described further below. The addition of the basic solution is continued until complete precipitation is achieved. The product of the precipitation can, if required, be stirred further, filtered off using conventional technical means and washed free of undesired water-soluble foreign ions.

The filtrate cake thus formed can be dried at from 50° to 200° C. and the material thus obtained can be milled. As an alternative, it is possible to slurry up the filter cake and subsequently spray dry the slurry in a spray drier at from 100° to 600° C. to give a spray-dried powder. If spray drying is chosen, the promoters manganese, phosphorus and/or alkali metals can also be added to the catalyst in the form of their salts in this process step.

The powders thus produced can be calcined, and the calcined powders can be shaped in various ways to give shaped bodies. Thus, it is possible to pelletize or extrude the powders or to compact them by means of an extruder to give extrudates of particular shape and size. In all cases, forming aids such as graphite or stearic acid can be mixed into the powder.

The calcination is carried out in one step at final temperatures of from 500° to 1000° C., preferably 800° to 1000° C., particularly preferably from 850° to 950° C.

For the reduction, the calcined catalysts are flushed with nitrogen at room temperature and a pressure of from 2 to 10 bar, preferably from 4 to 8 bar, is set under a nitrogen atmosphere.

Subsequently, generally from 2 to 30% of the nitrogen stream, preferably from 5 to 15%, is replaced by hydrogen and the temperature is increased, generally over a period of from 2 to 24 hours, preferably from 5 to 15 hours, from room temperature to from 80° to 200° C., preferably from 120° to 160° C. Then, in general, a further part of the nitrogen stream is replaced by hydrogen so that a total hydrogen content of from 30 to 70%, preferably from 40 to 60%, is achieved. Subsequently, the temperature is generally increased over a period of from 2 to 24 hours, preferably from 5 to 15 hours, to from 200° to 400° C., preferably from 250° to 350° C. This final temperature is generally maintained until no water of reduction can be detected in the gas stream leaving the catalyst. The hydrogen component in the gas stream is then generally again replaced by nitrogen and the reduced catalyst is allowed to cool to room temperature in the nitrogen stream.

For the surface oxidation of the reduced catalyst, air is gradually metered into the nitrogen stream so slowly that the temperature in the catalyst bed does not exceed 60° C., ie. from 20° to 60° C., preferably from 20° to 50° C., particularly preferably from 20° to 40° C. The replacement of nitrogen by air is continued until the gas stream flowing through the catalyst consists of 100% air.

This gives cobalt catalysts having a specific surface area of greater than or equal to 12 m²/g, ie. from 12 to 500 m²/g, preferably from 15 to 200 m²/g, particularly preferably from 18 to 100 m²/g, and a porosity of greater than or equal to 0.16 cm³/g, ie. from 0.16 to 1.00 cm³/g, preferably from 0.18 to 0.80 cm³/g, particularly preferably from 0.20 to 0.40 cm³/g.

As regards shape, it is possible to produce all geometric bodies which can be used to charge fixed-bed reactors.

Both unsupported and supported catalysts are suitable for hydrogenation. This also applies to the reaction of nitriles and imines with hydrogen to give the corresponding amines.

The catalysts of the invention are suitable as hydrogenation catalysts, particularly for reactions of nitriles and/or imines with hydrogen to give primary amines at from 60° to 150° C. and pressures of from 50 to 300 bar.

As a criterion for the chemical long-term stability (eg. the base stability), a test has been developed which allows a prediction about the operating life of a catalyst under reaction conditions to be made after only a short time.

This short test, referred to as autoclave test, can be carried out as follows:

A catalyst reduced with hydrogen above 200° C. and an aqueous base such as NaOH or KOH can be placed in an autoclave under an inert gas atmosphere and maintained at about 160° C. under an autogenous pressure of from about 5 bar for 12 hours. After cooling, decanting off the liquid and washing the catalyst with water, the hardness can be determined under an inert gas atmosphere, eg. under nitrogen.

A catalyst having a cutting hardness of greater than or equal to 30N, ie. from 30 to 1000N, preferably from 35 to 200N, particularly preferably from 40 to 100N, possesses, on the basis of experience, sufficient long-term stability in reactions in basic media (operating life>5000 hours).

EXAMPLES

Autoclave Test

A 250 ml autoclave fitted with Teflon insert was charged under nitrogen with 10 ml of catalyst in reduced form and 100 ml of a 2.5% strength by weight aqueous NaOH solution. The reduction of the catalyst had previously been carried out in a continuous apparatus with $H_2$ at 360° C. over a period of 5 hours. The closed autoclave was heated to 160° C., resulting in an autogenous pressure of about 5 bar. The temperature was maintained at 160° C. for 12 hours and, after cooling, the liquid was decanted off, the catalyst was washed with water and the hardness was subsequently determined under $N_2$.

Catalyst Preparation

The specified percentages by weight are based on the respective oxides in the ignited catalyst, the phosphorus content is given as $H_3PO_4$.

Catalyst A

Cobalt nitrate, manganese nitrate and phosphoric acid are dissolved in water to give a solution containing 10% by weight of cobalt, 0.55% by weight of manganese and 0.45% by weight of $H_3PO_4$. Precipitation was carried out at a temperature of 50° C. by addition of a 20% strength sodium carbonate solution. The precipitate formed was washed until sodium or nitrate could no longer be detected in the washing water. The solid thus obtained was slurried with water and spray dried in a spray drier (inlet temperature=550° C.). The spray-dried material was dried at 500° C., ground and mixed and shaped in an extruder to give extrudates having a diameter of 4 mm. The extrudates were dried at from 100° to 120° C. and calcined for 1 hour at 900° C.

For the reduction, the calcined catalyst was flushed at room temperature with nitrogen and a pressure of 6 bar was set under a nitrogen atmosphere. 10% of the nitrogen stream was then replaced by hydrogen and the temperature was increased from room temperature to 140° C. over a period of 10 hours. A further 38% of the nitrogen stream was then replaced by hydrogen so that a total hydrogen content of 48% was achieved. The temperature was subsequently increased over a period of 10 hours from 140° C. to 300° C.

This final temperature was maintained until water of reduction could no longer be detected in the gas stream leaving the catalyst. Subsequently, the hydrogen component of the gas stream was again replaced by nitrogen and the reduced catalyst was cooled to room temperature in the stream of nitrogen.

For the surface oxidation of the reduced catalyst, air was gradually metered into the nitrogen stream so slowly that the temperature in the catalyst bed did not exceed 60° C. The replacement of nitrogen by air was continued until the gas stream flowing through the catalyst consisted of 100% air.

The catalyst thus prepared contained 90.0% by weight of cobalt, 5.4% by weight of manganese, 2.8% of phosphorus and 0.16% of sodium and had a specific surface area of 21.3 m²/g and a porosity of 0.22 cm²/g.

Catalyst B (Comparative Catalyst)

This was prepared using a method similar to that for catalyst A, but after calcination the catalyst was not reduced in the stream of hydrogen and surface-oxidized in the stream of air. The catalyst thus prepared contained 90% by weight of cobalt, 5.2% by weight of manganese, 3% of phosphorus and 0.22% of sodium and had a specific surface area of 3.1 m²/g and a porosity of 0.13 cm³/g.

Catalyst C (Comparative Catalyst)

This was prepared using a method similar to that for catalyst A, but the catalyst was calcined for 1 hour at 650° C. and for 3 hours at 850° C. and then not reduced in the stream of hydrogen and surface-oxidized by treatment in the stream of air.

The catalyst thus prepared contained 90.4% by weight of cobalt, 5.1% by weight of manganese, 3.1% of phosphorus and 0.30% of sodium and had a specific surface area of 1.6 m²/g and a porosity of 0.11 cm³/g.

Test Procedure

A vertical tube reactor (diameter: 16 mm, fill height: 50 cm, oil-heated double jacket) was charged with 400 g (200 ml) of the catalyst A. The catalyst was activated under atmospheric pressure by passing through 200 standard l/h of hydrogen while increasing the temperature stepwise over a period of 24 hours from 100° to 340° C. and then maintaining the temperature at 340° C. for 24 hours.

80 g/h of isophoronenitrile (purity: 99.0%) and 270 g/h of liquid ammonia were pumped at 80° C. and a pressure of 250 bar from the bottom upwards through a tube reactor (diameter: 16 mm, fill height: 100 cm, oil-heated double jacket) connected upstream of the hydrogenation reactor, the tube reactor having been charged with 37 g (50 ml) of titanium dioxide in the form of 1.5 mm extrudates (weight hourly space velocity over the catalyst: 0.4 kg/l×h). Subsequently, 100 standard l/h (4.5 mol) of hydrogen were fed in and the product from the upstream imination reactor was passed from the bottom upwards through the hydrogenation reactor at 130° C. and a pressure of 250 bar. After letting down to atmospheric pressure, the ammonia was distilled off and the hydrogenation product was analyzed by gas chromatography.

The tests using the comparative catalysts B and C were carried out in a similar manner.

Catalysts have sufficient hydrogenation activity if the content of an intermediate referred to as aminonitrile is less than 500 ppm.

The results are shown in the following table:

| Catalyst | Cutting hardness autoclave test [N] | Surface area [m$^2$/g] | Porosity [cm$^3$/g] | Amino-nitrile [ppm] | Yield of isophorone-diamine [%] |
|---|---|---|---|---|---|
| A | 49 | 21.3 | 0.22 | <100 | 99 |
| B | 1 | 3.1 | 0.13 | 10000 | 95 |
| C | 20 | 1.6 | 0.11 | 200 | 99 |

We claim:

1. In a cobalt catalyst having a catalytically active composition comprising from 55 to 98% by weight of cobalt, from 0.2 to 15% by weight of phosphorus, from 0.2 to 15% by weight of manganese and from 0.5 to 5% by weight of alkali metal, calculated as oxide, as obtained by calcination of a powdery mixture of the active components in the form of their salts at a temperature of from 500° to 1000° C. and subsequent reduction in a stream of hydrogen at temperatures of from room temperature up to a final temperature of from 200° to 400° C., the improvement which includes a final step of surface-oxidizing said reduced catalyst by treatment in a stream of air at an elevated temperature up to not more than 60° C. and for a period of time sufficient to impart a catalyst life of more than 5000 hours as determined for a hydrogenation reaction carried out in a basic media.

2. A cobalt catalyst as claimed in claim 1, whose catalytically active composition comprises from 75 to 95% by weight of cobalt, from 0.5 to 10% by weight of phosphorus, from 2 to 10% by weight of manganese and from 0.1 to 3% by weight of alkali metal, calculated as oxide.

3. A cobalt catalyst as claimed in claim 1, whose catalytically active composition comprises from 85 to 95% by weight of cobalt, from 1 to 6% by weight of phosphorus, from 3 to 8% by weight of manganese and from 0.13 to 1% by weight of alkali metal, calculated as oxide.

4. A cobalt catalyst as claimed in claim 1, wherein the alkali metal used is lithium, sodium, potassium and/or cesium.

5. A cobalt catalyst as claimed in claim 1, which has a specific surface area of greater than or equal to 12 m$^2$/g and a porosity of greater than or equal to 0.16 cm$^3$/g.

6. A cobalt catalyst as claimed in claim 1, which has a cutting hardness of greater than or equal to 30N after carrying out an autoclave test for determining the base stability.

7. In a process for preparing amines by the catalytic reaction of hydrogen with nitriles and/or imines at a temperature of from 60° to 150° C. and a pressure of from 50 to 300 bar, the improvement which comprises carrying out said reaction in the presence of the catalyst obtained according to claim 1.

8. The catalyst obtained by the process of claim 1, wherein the final surface-oxidation step is carried out at a temperature of from 20° to 50° C.

9. The catalyst obtained by the process of claim 1, wherein the final surface-oxidation step is carried out at a temperature of from 20° to 40° C.

* * * * *